United States Patent [19]

Fleischauer

[11] Patent Number: 4,605,417
[45] Date of Patent: Aug. 12, 1986

[54] PROSTHETIC JOINT

[76] Inventor: K. E. Fleischauer, 2031 SE. 33rd St., Okeechobee, Fla. 33472

[21] Appl. No.: 657,370

[22] Filed: Oct. 3, 1984

[51] Int. Cl.$^4$ .............................................. A61F 2/66
[52] U.S. Cl. ..................................................... 623/49
[58] Field of Search ....................... 3/30, 33, 35, 32, 5, 3/6, 7

[56] References Cited

U.S. PATENT DOCUMENTS

| | | | |
|---|---|---|---|
| 608,812 | 8/1898 | Weller | 3/32 |
| 668,634 | 2/1901 | Gault . | |
| 757,287 | 4/1904 | Duggan | 3/35 |
| 1,144,681 | 6/1915 | Apgar . | |
| 1,151,144 | 8/1915 | Wofe et al. | 3/35 |
| 1,211,222 | 1/1917 | Pilling et al. . | |
| 1,285,871 | 11/1918 | Winn . | |
| 2,078,595 | 4/1937 | Barghausen . | |
| 2,357,893 | 9/1944 | Harrington . | |
| 2,430,584 | 11/1947 | Roche . | |
| 2,439,195 | 4/1948 | Witmyer et al. . | |
| 2,617,115 | 11/1952 | Ellery | 3/35 |
| 2,863,684 | 12/1958 | Carroll . | |
| 3,480,972 | 12/1969 | Prahl | 3/33 |
| 3,806,958 | 4/1974 | Gusev . | |
| 3,982,278 | 9/1976 | May . | |
| 4,413,360 | 11/1983 | Lamb . | |

FOREIGN PATENT DOCUMENTS 189337 3/1957 Fed. Rep. of Germany ............ 3/30

*Primary Examiner*—Richard J. Apley
*Assistant Examiner*—James Prizant
*Attorney, Agent, or Firm*—Steele, Gould & Fried

[57] ABSTRACT

A prosthetic ankle which can be easily and inexpensively manufactured and installed in conventional rigid prosthetic legs comprises opposing oblong plates having peripheries which are shaped to match the ankle portion of the leg in which the prosthetic ankle will be installed. Hinge structure bisects the inner surfaces of the plates and rotatably connects the plates, one of which is secured to a lower leg surface and the other to an upper foot surface. The plates may be sloped fore and aft to allow vertical rotation of the foot relative to the leg about the hinge axis. Biasing structure acts to return the foot to a position perpendicular to the leg and provide increased biasing with increased bending. The ankle allows small lateral rotations of the foot. The invention also provides for an auxiliary attachment, such that if an element of the ankle should fail the foot will remain secured to the leg.

20 Claims, 5 Drawing Figures

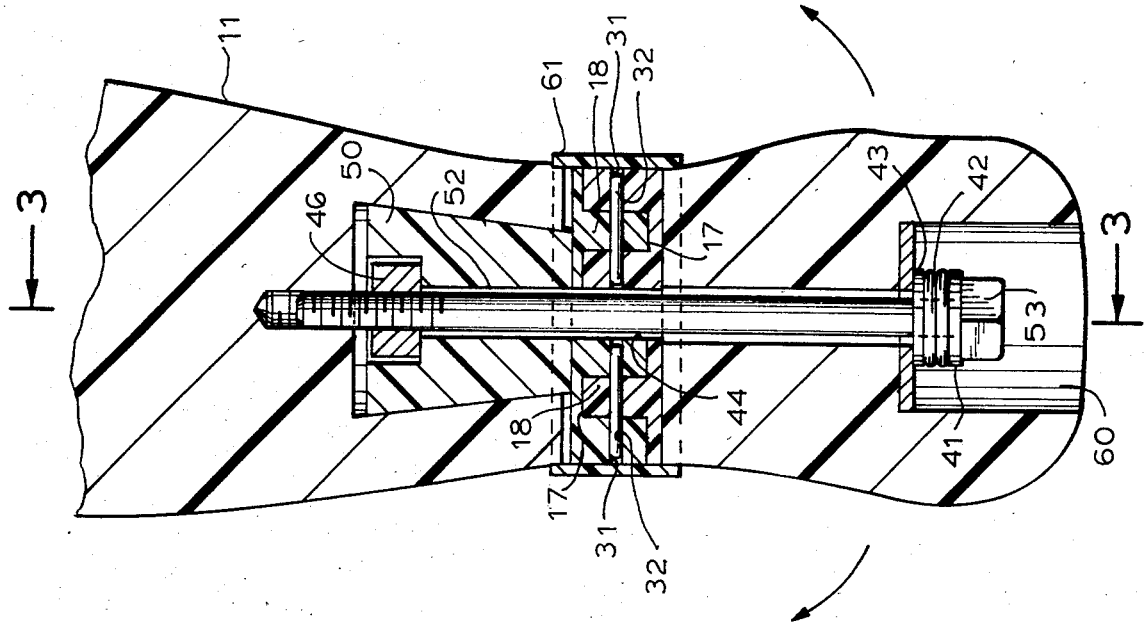
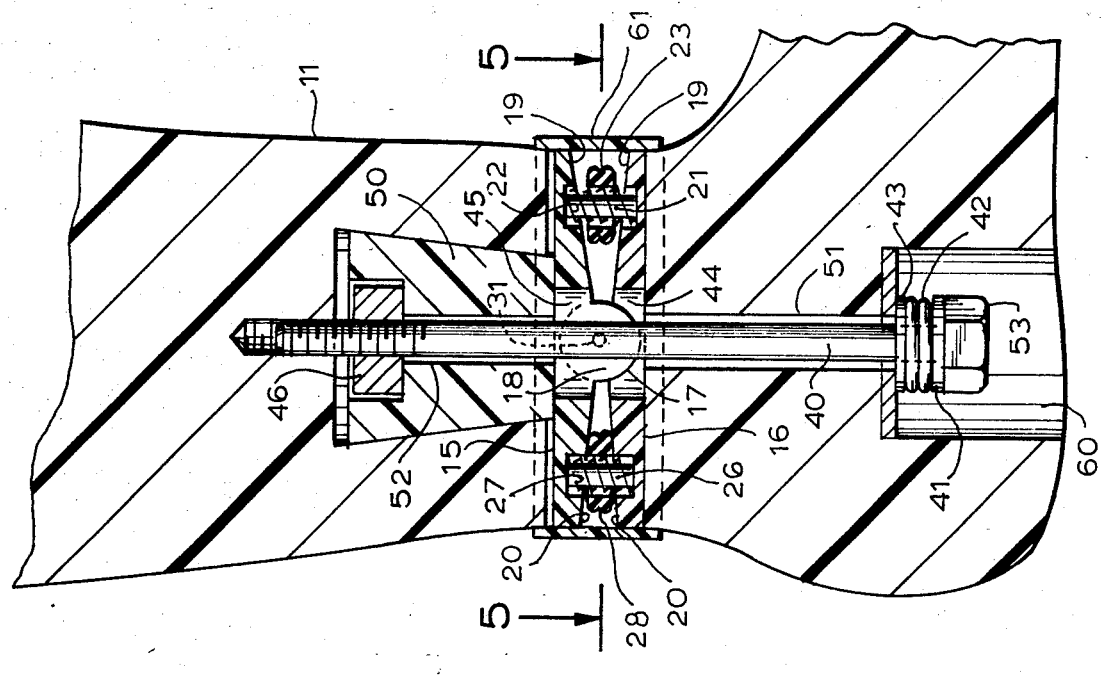

PROSTHETIC JOINT

BACKGROUND OF THE INVENTION

1. Field of the Invention

This invention relates generally to prosthetic joints, and specifically to a prosthetic ankle which is inexpensive, durable, life-like in operation, and can be easily and inexpensively installed into rigid prosthetic leg devices.

2. Description of the Prior Art

The ankle portion of prosthetic devices for both below-knee and above-knee amputees is conventionally rigid. A piece of shock absorbing substance such as rubber may be provided at the heel of the artificial foot to both absorb shock during walking and to provide some flexibility. However, this construction is a poor substitute for the natural movement of an ankle. The natural rocking motion afforded by an ankle smooths the walking motion and the body parts associated therewith help to absorb the shock forces that are associated with walking.

Prosthetic ankles have been provided for the amputee which seek to simulate the movement of the human ankle. These are quite expensive and usually require the purchase of a new leg and foot as they are commonly designed to cooperate with the ankle. These devices typically provide only a limited range of mobility, on the order of 3½° forward of the vertical axis and 1° backward. Previous ankle designs also provided little in the way of sideways give and therefore made walking laterally or sideways to an inclined surface difficult. Moreover, such designs often have no means for returning the foot to is natural position, perpendicular to the leg, without the application of external force. Those devices which do have internal biasing means are often either too restrictive and do not provide sufficient play or give, or are too loose and tend to flap about. Moreover, the biasing resistance which they provide is relatively constant over the full range of movement, limited though it is. It would be desirable to have more give at angles close to the vertical axis where fluctuations are common and more biasing at larger angles where greater support is needed. Previous prosthetic ankles have been very susceptible to wear and tend to work loose or deteriorate markedly with use. These failures of the prior art all contribute to a marked safety hazard in the use of prosthetic devices. Wobbling, and even falling, are everyday fears for the wearers of prosthetic leg devices.

The present invention provides a prosthetic ankle joint which is easily installed in conventional rigid prosthetic legs. The joint is inexpensively made and installed, and provides an extended range of movement, similar to that of the human ankle. The joint is internally biased to return the foot to a position perpendicular to the leg, and the biasing increases as bending increases. It is made of durable materials which can withstand the substantial forces which are placed on such a device.

SUMMARY OF THE INVENTION

It is an object of the present invention to provide a prosthetic ankle device which is easily incorporated into conventional, rigid artificial legs.

It is another object of the present invention to provide a prosthetic ankle device which is inexpensively made and installed in conventional, rigid artificial legs.

It is yet another object of the present invention to provide a prosthetic ankle device which closely simulates the range of motion afforded by the human ankle.

It is still another object of the present invention to provide a prosthetic ankle device which is biased to return the foot to a position perpendicular to the leg portion.

It is another object of the present invention to provide a prosthetic ankle device which provides relatively small resistance at leg-to-foot angles close to the perpendicular but affords greater biasing resistance as bending increases.

It is still another object of the present invention to provide a prosthetic ankle device which is durable when exposed to the severe forces which act on such a device.

It is yet another object of the present invention to provide a prosthetic ankle device which will safely secure the foot portion to the leg portion.

These and other objects are accomplished by providing a prosthetic ankle device which is formed by opposing upper and lower plates adapted for attachment to the lower leg portion and foot portions, respectively, of a conventional rigid prosthetic leg at its ankle portion. The plates are attached to each other by interfitted hinge means such that the natural rotations of the foot relative to the leg are permitted. The hinge means is preferably formed of projecting semicylindrical rings and grooves adapted to receive the rings. The rings have hollow cores which align when the rings are interfitted so as to receive a pin or pins which forms a hinge axis and holds the joint securely together.

Biasing means are located on the fore and aft side of the hinge joint which progressively resist rotation about the hinge axis. Each biasing member preferably comprises a rubber cylinder, the axis of which is perpendicular to the hinge axis and the top and bottom faces of which rest in seats formed in the plates. The biasing members further comprise springs, the coils of which loosely wrap the rubber cylinder. Means for stopping rotation are also provided. These means preferably comprise a rubber grommet further encircling both the spring and the cylinder.

The biasing means acts to return the foot to a position perpendicular to the leg, counteracting rotational forces with progressive resistance. The biasing means provides minor resistance to rotation about the hinge axis when the rotation is minor, such that the leg is substantially perpendicular to the foot. When bending becomes more extreme, however, increased resistance is provided as the cylinder acts on the spring and finally as the grommet is engaged by the plates. The hinge members and pins are precision formed with sufficient space therebetween to allow a small lateral rotation of the foot.

The ankle is preferably provided with a bolt which extends through a bore in the foot, slots in the plates, into a bore in the leg. The bolt head is seated on a grommet, and the bolt passes through a slot in the plates which extends fore and aft along a line perpendicular to the hinge axis and passing through the midpoint thereof. The grommet, slots and bores provide sufficient give around the bolt so that the afore described motions are permitted. The pins provide an added safety measure such that should a bolt shear, the foot will remain secured to the leg by the pins.

BRIEF DESCRIPTION OF THE DRAWINGS

There are shown in the drawings embodiments which are presently preferred. It should be understood, however, that the invention is not limited to the precise arrangements and instrumentalities shown.

FIG. 3 is a cross-section of the prosthetic ankle device taken along the line 3—3 in FIG. 4.

FIG. 4 is a cross-section of the prosthetic ankle device taken along the line 4—4 in FIG. 1.

DETAILED DESCRIPTION OF THE PREFERRED EMBODIMENTS

This invention provides a prosthetic ankle device which is inexpensively and easily installed in conventional rigid prosthetic legs. It provides fore and aft biasing such that the foot returns to a position perpendicular to the leg when no force is acting on it. Greater biasing forces are provided when the angular relationship between the foot and the leg is substantially off the perpendicular. A small lateral rotation of the foot is provided as by the human ankle. The construction materials are durable and can readily withstand the severe forces acting on the ankle. A safety feature can be provided so that the foot would be securely held to the leg even should an ankle element break.

Figure 1:
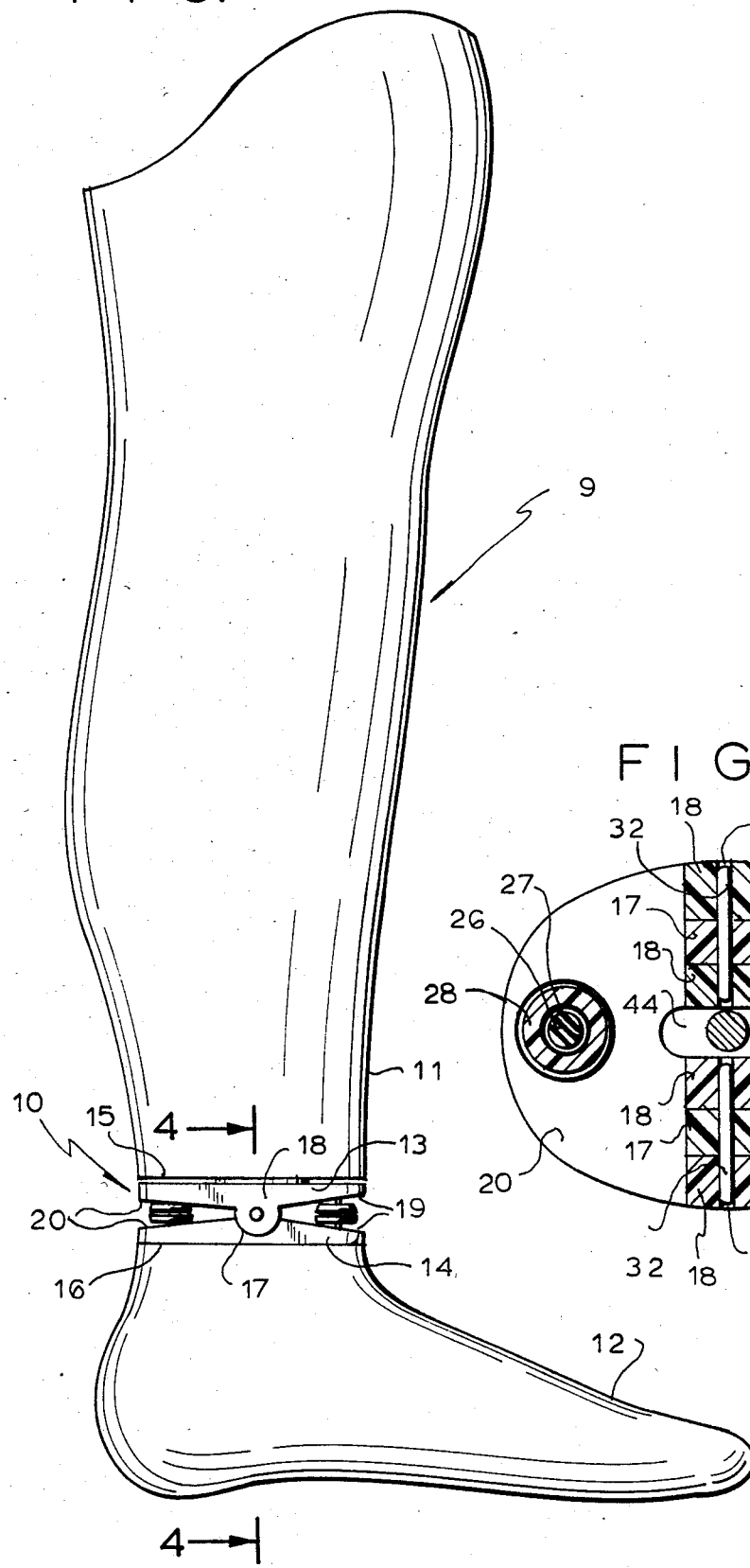
FIG. 1 is a side elevation of a prosthetic ankle device according to this invention.

The manner in which the preceding features and advantages are provided will be described with reference to the drawings. Like numbers in the drawings refer to like elements in the various figures. With reference to FIG. 1, a prosthetic leg 9 has a leg portion 11, an ankle 10, and a foot portion 12. The leg 11 and foot 12 are such as would be found in a conventional rigid prosthetic leg, where they would otherwise form a single rigid member. The ankle 10 has an upper plate 13 secured to the lower leg surface 15 and a lower plate 14 secured to an upper foot surface 16 in a manner to be described below.

Figure 2:
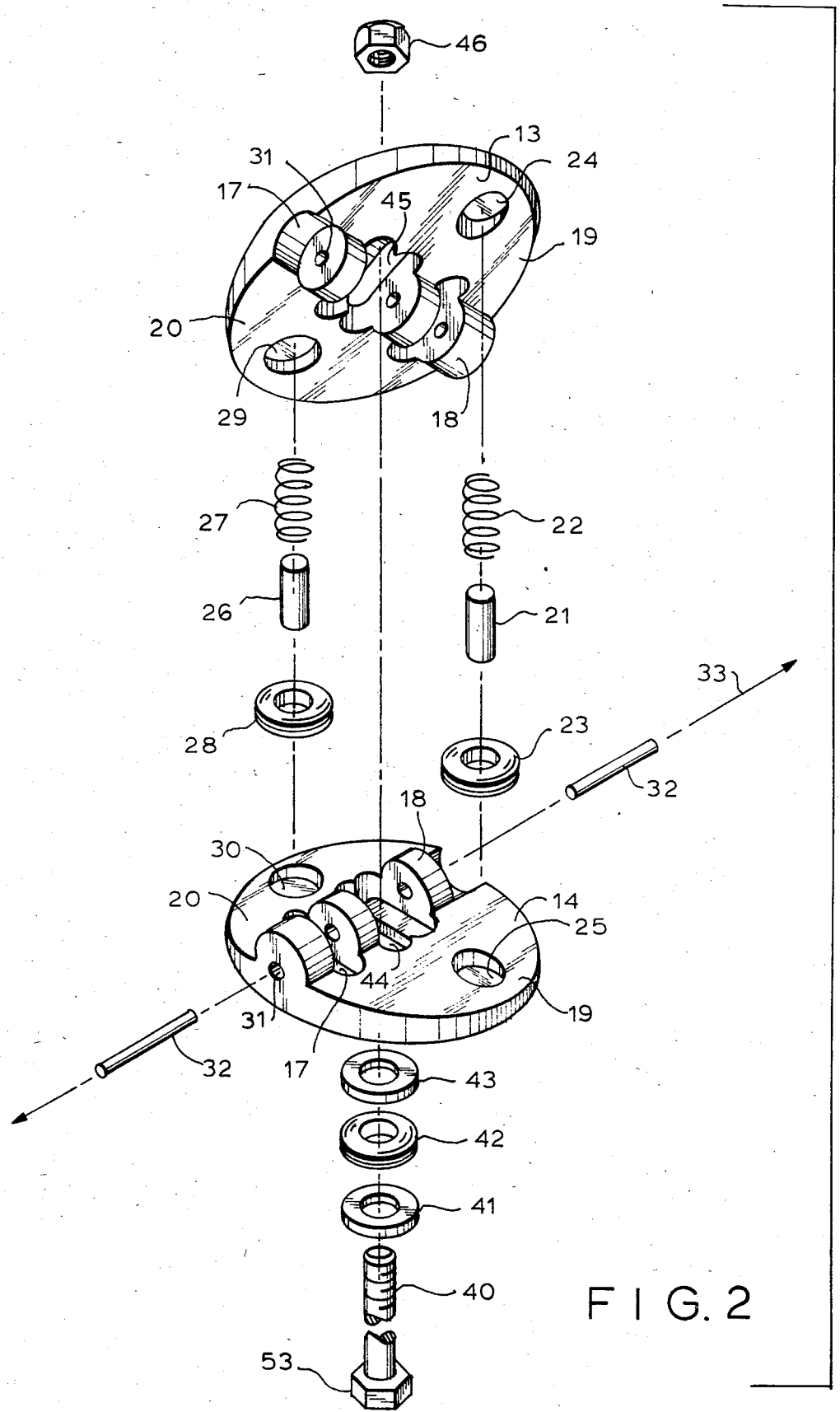
FIG. 2 is an exploded perspective view of the prosthetic ankle device shown in FIG. 1.

With reference now also to FIG. 2, the plates have hinge means formed therein which preferably comprises projecting semicylindrical rings 18 with hollow cores 31, the rings 18 alternating with recessed grooves 17 adapted to receive the rings from the opposing plate. The rings of the upper plate are disposed so as to be received by the grooves of the lower plate and to interfit with the rings of the lower plate. Similarly, the rings of the lower plate are received by the grooves of the upper plate when the rings are interfitted. When the rings are so interfitted, the cores 31 of the rings 18 align so as to form a bore through which are positioned pins 32 to hingeably secure the joint together. The location of the hinge axis 33 so formed should substantially duplicate the location of the axis of the human ankles, and more or less divides the plates into a fore half 19 and an aft half 20.

The plates 13 and 14 are preferably sloped fore and aft from the hinge axis such that the plates are narrower at their front and rear extremities. The opposing surfaces of the fore halves 19 and the aft halves 20 define included angles which represent the maximum allowable rotation about the hinge axis.

Biasing means are located fore and aft of the hinge axis 33. The biasing means preferably comprises, as forward of the hinge axis 33, a rubber cylinder 21 that is disposed perpendicularly to the hinge axis and preferably located on a line that bisects the hinge axis. A spring 22 is disposed over the cylinder 21 such that the coils of the spring 22 wrap around the cylinder 21. A grommet 23 encircles the spring 22 and the cylinder 21. The biasing means is mounted in an upper plate seat 24 and a lower plate seat 25. Similarly, the aft biasing means comprises rubber cylinder 26, spring 27 and grommet 28 resting in upper plate seat 29 and lower plate seat 30.

A bolt 40 used to secure the foot to the leg as an added safety feature in a manner to be described below. The bolt has associated therewith washer 41, rubber grommet 42, and washer 43. The bolt extends through slots 44 and 45 in the lower and upper plates, respectively, and is secured in a threaded unit such as nut 46 or the like, which is embedded in or otherwise secured to the leg portion 11 of the artificial leg 9.

Figure 5:
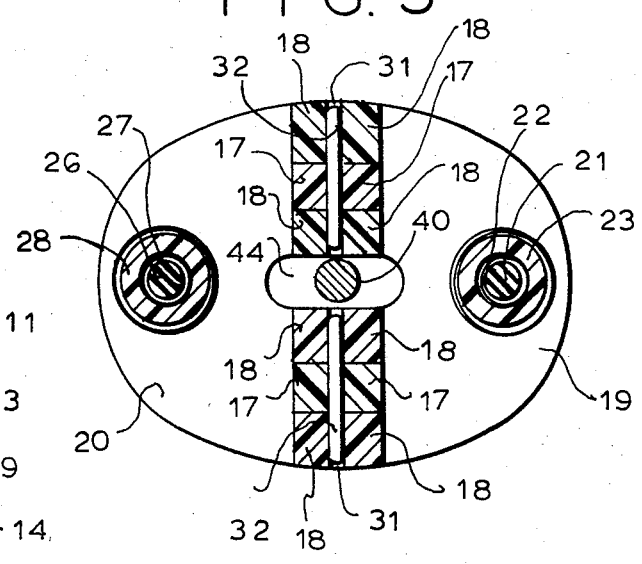
FIG. 5 is a cross-section of the prosthetic ankle device taken along the line 5—5 in FIG. 3.

In one embodiment, the nut 46 is in the nature of a helicoil and is embedded in a plug insert 50 which is centrally located in the base of the leg 11 (FIG. 3). The bolt 40 passes through a bore 51 which extends through the heel of the foot 12 and is aligned with the slot 44 in the lower plate 14 (FIG. 5) and the slot 45 in the upper plate 13. The bolt 40 continues through the bore 52 in the plug 50 and threadably engages the nut 46 which is embedded in the plug 50. The head 53 of the bolt 40, with washer 41, grommet 42, and washer 43, rest in a seat 60 hollowed from the heel of the foot 12.

One or both of the bores 51 and 52 will generally have a diameter in excess of the diameter of the bolt such that the bolt will have a range of motion within the bore when the foot is rotated. This design is preferable when a bolt made from an especially rigid material is used. The bores may have a substantially oval cross-section, aligned with the slots in the plates, as shown by the different clearances evident in FIGS. 3 and 4, which are oriented at right angles to one another about the longitudinal axis of the bolt.

During the walking motion, as the foot is lowered to the ground, the heel will commonly make contact first. This creates a force which acts to rotate the heel about the hinge axis 33 and to thereby move aft surfaces 20 towards one another. As this rotation takes place, cylinder 26 and spring 27 are compressed and thereby absorb some of the shock of impact. As the aft surfaces 20 move closer to one another, the cylinder 26 becomes larger in diameter as it is compressed. Its perimeter begins to press on the coils of the spring 27 such that compression of the spring coils is retarded and an increased biasing effect is created whereby further rotation about the hinge axis is more severely resisted. It can therefore be seen that when the leg is vertical and the foot is horizontal, there will be only minor resistance to bending, allowing a certain degree of freedom about the perpendicular. When bending is more severe, however, greater resistance is encountered, which helps to both align the foot relative to leg and also to absorb the shocks and strains which are associated with greater bending. As rotation of the plates continues, the aft surfaces 20 engage grommet 28 which gently stops further rotation without jarring.

The action of the biasing means in the fore half of the ankle is similar to that described above for the aft biasing means except that forward rotation should generally be more extensive than rearward rotation. The slope of the fore surfaces 19, and thus the included angle therebetween, is preferably greater than that of the aft surfaces 20 so that greater bending can occur in the forward direction than in the rearward direction. This action simulates that of the human ankle. Preferably, the sloped surfaces 19 coact with the fore biasing means to allow forward bending of the leg towards the foot of approximately 15°, while the aft sloped surfaces 20 and aft biasing means are so constructed as to allow approximately 6° rearward bendng. Greater bending increases the risk of falls as the center of gravity moves with bending away from a steady position directly above the feet.

It would be apparent to one skilled in the art that alternative means to stop rotation of the plates at a predetermined position could be used in place of the sloped surfaces and the grommet. For example, abutting surfaces at the fore and aft most peripheries could be fashioned into the plates to perform this function. Similarly, the slope of the plates could be reduced or eliminated altogether in favor of a larger hinge, which would allow a similar degree of rotation.

During the bending action, the bolt 40 moves forwards or rearwards in the slots 44 and 45 in one or both of the bores 51 and 52 such that the presence of the bolt does not interfere with the bending operation. Shear stresses brought on the bolt by the bending operation are absorbed partially by the grommet 42.

The hinge members 17 and 18, and pins 32 are built with sufficient tolerance to allow a small lateral rotation of the foot in either direction as indicated by the arrows in FIG. 4. This rotation is preferably approximately 2° in either direction from the vertical. As before, the bolt has sufficient lateral spacing in the slots 44 and 45 and in one or both of the bores 51 and 52 to allow this rotation, and any shear stress on the bolt is again partially taken up by the grommet 42.

The upper and lower plates are constructed preferably of nylon. Any durable plastic or other material which would be known to those skilled in the prosthetic art could be used. The cylinders 21 and 26, and the grommets 23, 28, and 42 can be made of any suitable elastomer which would be known to those skilled in the art. Preferable rubbers would be those known in the art as "80 gravity" rubbers. The springs 22 and 27, pins 32, bolt 40, washers 41 and 43, and nut 46, may be made of metals known to those skilled in the art, but preferably are fashioned from a quality stainless steel. The plug insert 50 is constructed as is known in the art but typically is made from willow wood.

Installation of the prosthetic ankle is simple and inexpensive. The prosthetic foot is removed from the leg approximately where the human ankle would be located. Approximately ¾ inch must be removed from the leg and approximately one-quarter inch must be removed from the foot to make room for the ankle. The plug 50 with the bore 52 and the nut 46 is inserted into a suitable space fashioned in the leg 11. Bolt seat 60 is fashioned in the heel of the foot 12 and the bore 51 is drilled through the foot. The lower plate 14 and upper plate 13 are installed at the top of the foot 16 and bottom of the leg 15 such that slots 44 and 45 align with the bolt bores 51 and 52.

The plates are secured to the leg and the foot through means known in the art. Preferably holes will be drilled as seats for screws (not shown in the drawings). The location of the holes is left to the discretion of the professional prosthetic installer, although a location between the biasing seats 24-25 and 29-30, and the slots 44 and 45 would do.

Once the plates are attached, the hinge members are interfitted with the biasing means in place and pins 32 are placed in the bores formed by cores 31. The pins 32 may include securing means known in the art such as split outer ends which wedge into the cores to secure the pins. The bolt 40 with washer 41, grommet 42, and washer 43 may then be slid through the bore 51, slots 44 and 45, into bore 52, and threadably engaged to nut 46 to thoroughly secure the foot 12 to the leg 11.

The presence of the bolt 40 is not necessary for operation of the invention. The pins 32 generally will be sufficient to hold the ankle together. It is an added safety feature which would hold the foot to the leg in the unlikely event that an element of the ankle device should fail.

A cosmetic covering 61 (FIG. 3) can be fitted around the prosthetic ankle to provide a more natural appearance. Such a covering would typically be made of pink vinyl and installed by methods known to those skilled in the art.

The present invention provides an inexpensive prosthetic ankle which can be easily and inexpensively installed in conventional rigid artificial legs. It is fashioned to allow bending similar to the range of motion allowed by the human ankle. It includes biasing means which absorb shock and act to return the foot to a natural position perpendicular to the leg. The biasing means are progressively resistant as more bending is encountered. Grommets stop bending, without jarring, at a point which simulates the range of motion of the human ankle but also helps to prevent loss of balance. The ankle is fashioned from durable materials which are nonetheless inexpensive to fashion and install. The pins are provided to insure that the foot remains attached to the leg in the unlikely event of a failure of an ankle element.

This invention may be embodied in other specific forms without departing from the spirit or essential attributes thereof, and accordingly, reference should be made to the appended claims, rather than to the foregoing specification, as indicating the scope of the invention.

What is claimed is:

1. A prosthetic ankle device for use with a rigid prosthetic lower leg portion and a rigid prosthetic foot portion, comprising:
   upper and lower plates adapted for attachment to flat faces on said lower leg and foot portions respectively, and disposed therebetween;
   said upper and lower plates having dual interfittable hinge means disposed along facing portions of said plates, said hinge means having complementary ridge and trough shapes which, when interfitted, bear against one another over a substantial area and define an axis of rotation for the foot portion relative to the lower leg portion, the axis being perpendicular to a plane of the leg portion and foot portion, said device further including:
   (a) longitudinally extending means from the leg portion to the foot portion which urges the ridge and trough shapes together, and
   (b) laterally extending means preventing separation of the ridge and trough shapes,
   said longitudinally extending means and said laterally extending means providing a safety measure in the event of failure of either of said means; and opposed biasing means located between said plates and spaced on both sides of said axis of rotation for progressively resisting said rotation about the axis, whereby natural foot rotation about an ankle is simulated with respect to cushioning of foot strikes without risking loss of balance.

2. The prosthetic ankle device of claim 1 wherein the complementary ridge and trough shapes are semicylindrical rings and grooves respectively.

3. The prosthetic ankle device of claim 1 wherein the means preventing separation includes at least one pin running transversely through the ridge and trough shapes.

4. The prosthetic ankle device of claim 1 wherein the means urging the ridge and trough shapes together includes a bolt disposed directly through the axis of rotation, the bolt having opposite ends affixed at the leg portion and foot portion, respectively, the plates having a through hole at a central portion of the hinge axis providing longitudinal and transverse clearance for the bolt.

5. The prosthetic ankle device of claim 4 wherein the bolt is readily accessible for adjustment purposes.

6. The prosthetic ankle device of claim 1, further comprising means for limiting rotation in a backward direction more than in a forward direction, whereby the risk of toppling backwards is reduced without limiting forward rotation, whereby a full range of natural foot movement may be safely achieved.

7. The prosthetic ankle device of claim 6, wherein said upper and lower plates have two pairs of opposing surfaces, one pair on each side of said axis, said pairs of surfaces defining oppositely directed included angles, said included angles defining the range of rotation about the axis.

8. The prosthetic ankle device of claim 7, wherein one of the included angles is smaller than the other at their respective maxima.

9. The prosthetic ankle device of claim 1, wherein the biasing means comprises substantially incompressible members for limiting rotation in a backward direction more than in a forward direction.

10. The prosthetic ankle device of claim 1, wherein said biasing means comprises a cylinder constructed of an elastomeric material around which are wrapped the coils of a spring, an elastomeric grommet encircling said spring and said cylinder, said cylinder being seated in bores in said upper plate and said lower plate adapted to receive said cylinder.

11. The prosthetic ankle device of claim 10, wherein said coils of said springs surrounding said cylinders are fitted such that they are engaged by the sides of said cylinders as said cylinders are compressed during a rotation, offering greater resistance to rotation as compression of the cylinder increases.

12. The prosthetic ankle device of claim 1, wherein said lower leg can be rotated backwards with respect to said foot approximately 6°.

13. The prosthetic ankle device of claim 1, wherein said leg can be rotated forward with respect to said foot approximately 15°.

14. The prosthetic ankle device of claim 1, wherein said foot can rotate laterally with respect to said leg approximately 2° from the vertical.

15. A prosthetic ankle device adapted for retro-attachment to a prosthetic leg having lower leg, ankle and foot portions, and from which at least a part of the ankle portion has been removed to separate the lower leg and foot portions from one another and define respective facing surfaces, the ankle device comprising:

upper and lower plates conforming in shape and adapted for attachment to said facing surfaces of said lower leg and foot portions, repectively and disposed therebetween, said upper and lower plates having interfittable hinge means respectively across said plates, said hinge means, when interfitted, defining an axis of rotation for the foot portion relative to the lower leg portion and including laterally extending means for securing said interfittable hinge means to each other;

biasing means disposed between said plates and on both sides of said axis for progressively resisting said rotation about said axis, whereby natural foot rotation about an ankle is simulated with respect to cushioning of foot strikes without risking loss of balance; and, auxiliary means for securing said foot portion to said lower leg portion of said prosthetic leg extending longitudinally through the center of said axis of rotation while allowing said rotation, said auxiliary means providing both a safety measure and a further means of adjustment.

16. The prosthetic ankle device of claim 15, wherein said upper and lower plates have two pairs of opposing surfaces, one pair on each side of said axis, said pairs of surfaces defining oppositely directed included angles, said included angles defining the range of rotation about the axis.

17. The prosthetic ankle device of claim 15, wherein said auxiliary means for securing said foot portion to said lower leg portion comprises a slot disposed fore and aft along and through each of said upper and lower plates, a first bore extending through the heel of said foot portion to said slot through said lower plate and a second bore extending from said slot through said upper plate into said lower leg portion, a threaded unit adapted to receive a bolt disposed at the closed end of said second bore, a bolt passing into said heel and through said first bore, said slots and said second bore, said bolt being secured in place by said threaded unit, and resilient means disposed between the bolt head and said first bore, relative movement of said bolt and said slots due to pivoting of the bolt about the resilient means accomodating the full range of the natural foot rotation, whereby the lower leg and foot portions may be securely connected without impairing operation of the device.

18. The prosthetic ankle device of claim 15, wherein said hinge means comprise semicylindrical rings defining an annular portion and a hollow core portion, said rings projecting from said inner surfaces and alternating with grooves in said inner surfaces adapted to receive said rings, such that, when interfitted, said rings of said upper plate are received by said grooves of said lower plate, and said rings of said lower plate are received by said grooves of said upper plate, said core portions of said rings being aligned to form a hinge axis, and at least one pin disposed through said core portions along said hinge axis to rotatably secure said hinge members together.

19. The prosthetic ankle device of claim 18, wherein said hinge means are fitted with sufficient tolerances to each other and to said at least one pin to allow a small lateral rotation of said lower plate in either direction with respect to said upper plate.

20. The prosthetic ankle device of claim 15, wherein said biasing means comprises a cylinder constructed of an elastomeric material around which are wrapped the coils of a spring, an elastomeric grommet encircling said spring and said cylinder, said cylinder being seated in bores in said upper plate and said lower plate adapted to receive said cylinder.

* * * * *